United States Patent
Sieger et al.

(10) Patent No.: US 12,302,906 B2
(45) Date of Patent: May 20, 2025

(54) FEED STUFF FOR BENEFICIAL ORGANISMS THAT CAN BE USED IN INTEGRATED PEST MANAGEMENT

(71) Applicant: E-NEMA GESELLSCHAFT FÜR BIOTECHNOLOGIE UND BIOLOGISCHEN PFLANZENZCHUTZ GMBH, Schwentinental (DE)

(72) Inventors: Sabrina Sieger, Barsbek (DE); Laurent Seychelles, Mauguio (FR)

(73) Assignee: E-NEMA GESELLSCHAFT FÜR BIOTECHNOLOGIE UND BIOLOGISCHEN PFLANZENZCHUTZ GMBH, Schwentinental (DE)

( * ) Notice: Subject to any disclaimer, the term of this patent is extended or adjusted under 35 U.S.C. 154(b) by 652 days.

(21) Appl. No.: 17/631,659

(22) PCT Filed: Jun. 26, 2020

(86) PCT No.: PCT/DE2020/100556
§ 371 (c)(1),
(2) Date: Jan. 31, 2022

(87) PCT Pub. No.: WO2021/018342
PCT Pub. Date: Feb. 4, 2021

(65) Prior Publication Data
US 2022/0272984 A1  Sep. 1, 2022

(30) Foreign Application Priority Data
Jul. 31, 2019 (DE) .................... 10 2019 120 647.2

(51) Int. Cl.
*A01N 63/12* (2020.01)
*A01K 67/30* (2025.01)

(52) U.S. Cl.
CPC .............. *A01N 63/12* (2020.01); *A01K 67/30* (2025.01)

(58) Field of Classification Search
CPC ............................. A01N 63/12; A01K 67/033
See application file for complete search history.

(56) References Cited

FOREIGN PATENT DOCUMENTS

WO    2013190143    12/2013

OTHER PUBLICATIONS

Honnens et al. (Aquacult Int (2014) 22: 399-409).*
Beneficial Insects (2015).*
Azevedo et al., "Free living nematodes as alternative prey for soil predatory mites: An interdisciplinary case study of conservation biological control", Biological Control, vol. 132, pp. 128-134. San Diego, CA.
Ricci et al., "Desiccation of Panagrolaimus rigidus (Nematoda): survival, reproduction and the influence on the internal clock", Hydrobiologia, vol. 347, pp. 1-13. 1997.
Salehian et al., "The importance of feeding status and desiccation rate in successful anhydrobiosis of Panagrolaimus detritophagus", Nematology, vol. 13, No. 2. pp. 185-191. 2011.
Honnens et al., "Desiccation and storage of *Panagrolaimus* sp. (strain NFS-24-5)", Nematology, vol. 15, No. 5. pp. 557-566. 2013.
Honnens et al., "Liquid culture of *Panagrolaimus* sp. for use as food for marine aquaculture shrimp and fish species", Nematology, vol. 15, No. 4. pp. 417-429. 2012.
Carrillo et al. (editors), "Prospects for Biological Control of Plant Feeding Mites and Other Harmful Organisms" (book), Chapter 2 Moraes et al, pp. 33-75 and Chapter 4 Azevedo et al., pp. 103-132. 2015.
Hilgers et al., "Artemia sp. Cysten als Aufzuchtfutter für Macrolophus pygmaeus: eine Evaluation unter Praxisbedingungen", Gesunde Pflanzen, vol. 68, Issue 3. pp. 135-143. 2016.

* cited by examiner

Primary Examiner — Shirley V Gembeh
(74) Attorney, Agent, or Firm — Jordan IP Law, LLC

(57) ABSTRACT

The invention relates to the use of *Panagrolaimus* sp. for feeding useful insects or in a method for controlling plant-damaging arthropods by applying a *Panagrolaimus* sp.-containing, useful insect- and mite-promoting feed stuff at the location of at least one plant species.

10 Claims, 1 Drawing Sheet

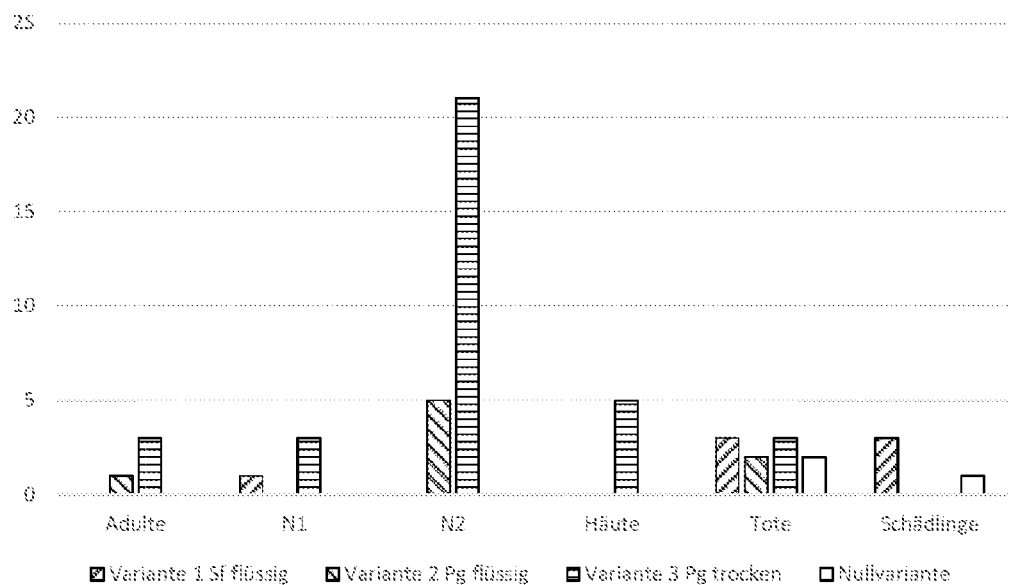

FEED STUFF FOR BENEFICIAL ORGANISMS THAT CAN BE USED IN INTEGRATED PEST MANAGEMENT

CROSS-REFERENCE TO RELATED APPLICATIONS

This application represents the U.S. National Phase of International Application number PCT/DE2020/100556, entitled "Feed Stuff for Beneficial Organisms that can be used in Integrated Pest Management", filed on 26 Jun. 2020, which claims benefit to German patent document DE102019120647.2 filed Jul. 31, 2019, all of which are incorporated herein by reference.

BACKGROUND OF THE INVENTION

The invention relates to a feed stuff for beneficial organisms that can be used in integrated pest management.

In integrated pest management (IPM), biological pest management with beneficial organisms, also known as beneficials, plays a very important role. In the Pest Management Act, integrated pest management is defined as a "combination of processes in which the use of chemical pesticides is restricted to the necessary extent, taking into account biological, biotechnical, plant-breeding, cultivation and cultural measures as priorities."

Many plant pests and pathogens can be combated with biological pesticides or beneficial organisms. There are currently more than 80 commercially produced beneficial species (insects, mites and nematodes) against pests available to professional horticulture. Their use can reduce the amount of chemical pesticides used and still ensure efficient and environmentally friendly pest management. The particular advantage of biological pest management methods is that they do not leave any undesirable residues on the crop.

It is common practice in beneficial organism breeding to feed omnivorous beneficial organisms with special rearing feed. For example, for the rearing of *Macrolophus* predatory bugs, the use of sterilized eggs from the flour moth *Ephestia kuehniella* and the cereal moth *Sitotroga cerealella* has proven useful as a basic food source. However, because of their perishability, these feed stuffs cannot be stored for a long time, so that the use of these feed stuffs is labor-intensive and costly.

As an alternative, the saltwater shrimp of the *Artemia* genus has been used for several years as a supplement to the feeding strategy. The development of the predatory bug *Orius laevigatus*, which is used in biological pest management, is comparable to the use of the conventional feeding system based on *Ephestia kuehniella* when it is fed with decapsulated *Artemia* cysts. However, when used in establishing the predatory bug *Macrolophus pygmaeus*, feeding with *Artemia* cysts alone proves to be of poor quality in terms of survival, growth and weight rates, a supplementary feeding in combination with *Ephestia kuehniella* producing satisfactory results (Hilgers, J., N. Gruda, and G. Noga, 2016. *Artemia* sp. cysts as rearing fodder for *Macrolophus pygmaeus*: an evaluation under practical conditions. Gesunde Pflanzen. [Healthy Plants] 135-143). Nevertheless, in terms of shelf life, this feed stuff has consistently more favorable properties than eggs from *Ephestia kuehniella* and *Sitotroga cerealella*.

90% of *Artemia* world production is obtained as dry cysts from the Great Salt Lake in the USA (FAO, Cultured Aquatic Species Information Program: *Artemia* spp (Leach, 1819), Food and Agriculture Organization of the United Nations, Editor. 2014, Fisheries and Aquaculture Department: Rome, Italy). The remaining 10% of world production is spread across northern and central China, southern Siberia, southern Vietnam and northeastern Brazil. The European Union does not have its own production and is therefore 100% dependent on imports from abroad.

Because production is limited to naturally occurring populations in salt lakes and (local) climate-related phenomena, such as the El Nino phenomenon, global crop yields fluctuate greatly. In addition, fresh water is a basic requirement for the production of *Artemia*, whereby a water shortage caused by climate changes, such as in China, leads to an increasing salt content in the salt lakes, which has a negative effect on *Artemia* production.

From an ecological point of view, a major disadvantage of using *Artemia* is the wild capture of *Artemia*, which damages the ecosystems that are also home to many bird species. Moreover, the *Artemia* cysts available on the market are chemically treated for the decapsulation process, which creates environmentally harmful waste products.

In order to conserve natural resources, reduce interference in ecosystems and avoid environmentally harmful processing methods in feed stuff production, there is a need for high-quality feed alternatives of the same quality. The object of the invention is therefore to create a feed alternative to feeding with *Artemia* for beneficial insects and mites that can be used in integrated pest management.

SUMMARY OF THE INVENTION

This object is achieved according to the invention by the use having the features of claim 1. The dependent claims reflect advantageous embodiments of the invention.

The basic idea of the invention is to use nematodes of the genus *Panagrolaimus* sp. as a feed and rearing medium in beneficial organism breeding and for better establishment of beneficial organisms in horticulture.

In particular, the invention is based on the observation that the various nymph stages and the adult forms of *Macrolophus* sp. exhibit rapid development, especially with killed and dried nematodes of the genus *Panagrolaimus* as a feed resource. Furthermore, it was possible to show in experiments that other omnivorous beneficial insects, such as *Orius* sp. or *Adalia* sp., were able to build up a population because of the nematode feed resource according to the invention.

Members of the genus *Panagrolaimus* (order Panagrolaimidae) are non-parasitic, bacteria-eating nematodes that occupy various terrestrial niches. A special feature is their anhydrobiosis capability, a survival under almost complete dehydration, wherein the metabolism is completely stopped. Once resupplied with water, the animals become active again after a short time and resume their original vital functions.

If nematodes of the genus *Panagrolaimus* sp. are exposed to unfavorable environmental conditions (dehydration or temperatures below freezing point), they begin to dehydrate and store unordered proteins (LEA and TDP proteins) as well as non-reducing disaccharides (trehalose and sucrose) and glycerol in the cells. The disaccharides support the vitrification of the inner cell environment and replace water in the cell membranes. This process leads to a kind of bioglass, an amorphous organic framework that shuts down all metabolic processes and protects cell contents and cell membranes.

Compared to the use of *Artemia*, *Panagrolaimus* has the advantage as a feed and rearing medium for beneficial insects that *Panagrolaimus* sp. naturally contains essential fatty acids that are not found in Anemia. In addition, there is the possibility of enriching the nematodes with other nutrients that are beneficial or even essential for the beneficial organisms used in integrated pest management.

The production of *Panagrolaimus* sp. is possible, for example, in monoxenic liquid culture in the bioreactor under sterile and controlled conditions with constant quality of the nematodes. Compared to wild-caught *Artemia*, large-scale production in bioreactors is possible, which is a significant advantage.

According to the invention, the use of *Panagrolaimus* sp. for feeding beneficial organisms, in particular beneficial insects (*Insecta*) and spiders (*Arachnida*) defined as beneficial organisms is proposed, the use being aimed in particular at feeding bugs (Heteroptera) used as beneficial insects. Targeted toward ladybugs (Coccinellidae) and mites (*Acari*).

The beneficial organisms benefiting from the present invention include, among the insects, the orders Coleoptera, especially with the aforementioned ladybugs and rove beetles (Staphylinidae), *Hemiptera/Heteroptera*, in particular with the plant bugs and flower bugs, and Neuroptera, especially with the lacewing family (Chrysopidae). The beneficial organisms relating to spiders relate in particular to the order of the mites, specifically with the families Phytoseiidae, Cheyletidae, Laelapidae and Macrochelidae.

The invention is suitable in particular for feeding plant bugs (Miridae), especially *Macrolophus* sp., and flower bugs (Anthocoridae), especially *Orius* sp., or ladybugs of the genus *Adalia, Harmonia, Coccinella* or *Cryptolaemus* spp. Most preferred is *Panagrolaimus* sp., which is used to feed the plant bug *Macrolophus pygmaeus* and the flower bug *Orius laevigatus*. Among the preferred mites fed with *Panagrolaimus* sp. are the genera *Phytoseiulus, Amblyseius*, and *Hypoaspis*.

The likewise proposed method for controlling arthropods which are harmful to plants is connected to the use of *Panagrolaimus* sp. as feed stuff for beneficial insects. For this purpose *Panagrolaimus* sp. is applied as feed stuff at the location of at least one plant and serves as additional feed in addition to the plant pests. An effective control of the pests and an adequate pest management is achieved indirectly by feeding the beneficial organisms. These pests include, in particular, mealybugs (Pseudococcidae). Whiteflies (Aleyrodoidea), butterflies (Lepidoptera), *thrips* (Thysanoptera), spider mites (Tetranychidae) and springtails (Collembola).

Live individuals of *Panagrolaimus* sp. are applied as feed stuff. Individuals of the genus *Panagrolaimus* sp. can also be fed in dried and preferably also shredded form. This form of administration has proven to be particularly beneficial for the beneficial organisms.

The method is suitable in particular for growing tomatoes (*Solanum lycopersicum*) or peppers (*Capsicum* sp.) outdoors and under glass.

Finally, a feed stuff is proposed for feeding insects which has individuals of the genus *Panagrolaimus* sp. in dried and preferably shredded form, and most preferably in calendered form. The feed stuff, which is also used for the method according to the invention, can in particular exclusively have—that is, can in particular consist exclusively of—individuals of the genus *Panagrolaimus* sp.

The feed stuff preferably contains adult individuals of the genus *Panagrolaimus* sp. having an average length of 900 to 1,100 µm and an average diameter of 35 to 55 µm, and more preferably juvenile individuals of the genus *Panagrolaimus* sp. having an average length of 200 to 400 µm and an average diameter of 15 to 25 µm.

BRIEF DESCRIPTION OF THE FIGURE

FIG. 1 shows the result of an experiment with examples.

DETAILED DESCRIPTION OF THE PREFERRED EMBODIMENTS

The invention is explained in greater detail below with reference to a particularly preferred embodiment.

The use of *Panagrolaimus* sp. as a feed resource was examined in the protected tomato cultivation in the greenhouse.

Tomatoes are among the most widely consumed vegetables in the world. In 2016, more than 177 million tomatoes were grown globally. The production of tomatoes is >33% higher than ten years ago. The importance of tomato cultivation is increasing, and with it the importance of biological pest management to ensure that tomatoes can be grown reliably.

In the present case, truss tomatoes of the Briozo RZ F1 variety were planted in plastic pots of 9 with a peat-free coconut substrate. The tomato plants were grown in the greenhouse at natural length of day (+/−at 18-24° C. day temperature, 18-20° C. night temperature). After 6 weeks of preculture, the thick shoots of the plants were trimmed to about 20 cm, each plant obtaining 3 pairs of leaves. 20 tomato plants were individually provided with a plexiglass hood and gauze for air circulation, in each case five plants being set up in a block design.

At the start of the experiment, the tomato plants in all 4 variants were equipped with 10 vital and equally sized adult individuals of the species *Macrolophus pygmaeus*.

*Macrolophus pygmaeus* is an omnivorous insect that has made a name for itself as a beneficial organism in professional tomato cultivation based on its good feeding performance and its broad host range. The bug, which has very high acquisition and rearing costs, is used in pepper and tomato crops to control whiteflies, caterpillars and spider mites. Fluctuations in the pest population can lead to a lack of forage and the population of *Macrolophus pygmaeus* can build up only with difficulty. A build-up of the *Macrolophus pygmaeus* population by supplementary feeding is therefore desirable under normal practical conditions.

The *Macrolophus pygmaeus* individuals placed on the tomato plants were fed weekly for 5 weeks as follows:

According to feed variant 1, living nematodes of the species Steinernema feltiae were dissolved in water as feed stuff and applied dropwise, 3 drops per leaf, to the plants.

According to feed variant 2, living individuals of the species *Panagrolaimus* sp. in dehydrated form were used as a food source, also dissolved in water and applied dropwise to the plants.

The nematode *Panagrolaimus* sp., was also used in feed variant 3, but in dried and shredded form. For this purpose, the dried and shredded material was distributed over 3 small places per sheet.

Finally, the control batch, in which the plants were left without adding insect food, was designated as feed variant 4.

For the production of the feed comprising the nematode *Panagrolaimus* sp., *Panagrolaimus* sp. NFS 24-5 was cultivated as a monoxenic liquid culture for eight days in the fermenter under sterile conditions. Bacteria were used as a food source. For harvesting, the nematodes were concentrated using sieves and the concentrated nematode paste obtained thereby was dried. The dried nematodes were then shredded. The dried and shredded end product was stored at a room temperature of 4° C.

Before each weekly feeding, the 20 plants, complete with leaves and stem, were assessed. The scoring included the count of living and dead *Macrolophus pygmaeus* nymph stages, adult individuals, visible exuvia, harmful organisms and the appearance of food residues. The first assessment took place in week 17, the last assessment took place in week 20.

The result of the experiment with examples is shown in FIG. 1.

On tomato plants which had been treated according to feed variant 1, a total of one nymph of the stage NI of *Macrolophus pygmaeus* was found on a single tomato plant. The nymph was very poorly developed, only the dead remains of the originally used *Macrolophus pygmaeus* individuals being detectable on the remaining four tomato plants.

Overall, the tomato plants had pests, namely mealybugs (Pseudococcidae), *thrips* (Thysanoptera) and springtails (Collembola).

If, on the other hand, the tomato plants were treated according to feed variant 2 (live *Panagrolaimus* sp. as a food source), nymphs of stage N2 were found on each plant, an adult individual also being present. No pests could be observed.

Feed variant 3, in which dry and shredded *Panagrolaimus* sp. were used, was able to achieve a clear improvement compared to feed variant 2. On average, four N2 nymphs were found here, all of which appeared to be very well developed and vital. There were also three adult individuals on two plants. No pests could be observed here either.

In the control batch, i.e., without additional feed introduced for *Macrolophus pygmaeus*, no living adult animals or nymphs of *Macrolophus pygmaeus*, but some pests, could be found.

The experiment clearly shows that the use of *Panagrolaimus* sp. as a feed stuff leads to an increased vitality of the beneficial organisms and a decrease in plant pests. This effect is surprisingly observed most intensively when dried and shredded *Panagrolaimus* sp. is used.

The invention claimed is:

1. A method comprising:
 feeding *Panagrolaimus* sp to a bug (Heteroptera) or a ladybug (Coccinellidae).

2. The method according to claim 1, wherein the bug is a plant bug (Miridae) or a flower bug (Anthocoridae).

3. The method according to claim 2, wherein the plant bug is *Macrolophus* sp. and the flower bug is *Orius* sp.

4. The method according to claim 3, wherein the plant bug is *Macrolophus pygmaeus* and the flower bug is *Orius laevigatus*.

5. The method according to claim 2, wherein the plant bug is *Macrolophus pygmaeus* and the flower bug is *Orius laevigatus*.

6. The method according to claim 1, wherein the ladybug is *Adalia, Harmonia*, Coccinella or *Cryptolaemus* spp.

7. A method for controlling arthropods which damage plants, comprising applying a feed stuff having *Panagrolaimus* sp. and promoting beneficial insects at the location of at least one plant species, wherein the individuals of the genus *Panagrolaimus* sp. are shredded.

8. The method according to claim 7, wherein the arthropods are selected from the group consisting of mealybugs (Pseudococcidae), whiteflies (Aleyrodoidea), butterflies (Lepidoptera), *thrips* (Thysanoptera), spider mites (Tetranychidae) and springtails (Collembola).

9. The method according to claim 8, wherein the plant is a tomato (*Solanum lycopersicum*) or a pepper (*Capsicum* sp.).

10. The method according to claim 7, wherein the plant is a tomato (*Solanum lycopersicum*) or a pepper (*Capsicum* sp.).

* * * * *